United States Patent [19]
Rolf

[11] Patent Number: 5,889,029
[45] Date of Patent: Mar. 30, 1999

[54] USE OF COTININE IN TREATING PSYCHIATRIC DISORDERS

[75] Inventor: David Rolf, Eden Prairie, Minn.

[73] Assignee: LecTec Corporation, Minnetonka, Minn.

[21] Appl. No.: 969,767

[22] Filed: Nov. 13, 1997

Related U.S. Application Data

[62] Division of Ser. No. 688,363, Jul. 30, 1996, Pat. No. 5,776,956.

[51] Int. Cl.⁶ .................................................. A61K 31/465
[52] U.S. Cl. .............................................................. 514/343
[58] Field of Search .............................................. 514/343

[56] References Cited

U.S. PATENT DOCUMENTS

| | | | |
|---|---|---|---|
| 3,870,794 | 3/1975 | Hutchinson et al. | 424/264 |
| 4,946,853 | 8/1990 | Bannon et al. | 514/343 |
| 5,187,169 | 2/1993 | Lippiello et al. | 514/343 |
| 5,298,257 | 3/1994 | Bannon et al. | 424/449 |
| 5,596,007 | 1/1997 | Keenan et al. | 514/343 |
| 5,612,357 | 3/1997 | Keenan et al. | 514/343 |
| 5,643,928 | 7/1997 | Keenan et al. | 514/343 |

FOREIGN PATENT DOCUMENTS

| | | |
|---|---|---|
| 273715 | 8/1962 | Australia . |

OTHER PUBLICATIONS

Freedman R., Hall M., Adler LE, Leonard S. "Evidence of Postmortem Brain Tissue for Decreased Numbers of Hippocampal Nicotinic Receptors in Schizophrenia", *Biol. Psychiatry*, 38(1):22–33 (1995).

Newhouse, P.A., Potter A., Corwin J., Lenox R., "Age–related Effects of the Nicotinic Antagonist Mecamylamine on Cognition and Behavior", *Neuropsychopharmacology*, 10(2): 93–107 (1994).

McConville B.J., Sanberg P.R., Fogelson M.H., et al. "The Effects of Nicotine Plus Haloperidol Compared to Nicotine Only and Placebo Nicotine Only in Reducing Tic Severity and Frequency in Tourette's Disorder", *Biol. Psychiatry* 31(8): 832–840 (1992).

Rosecrans JA. "The Role of Nicotine in Tobacco Dependence and Cessation", *Chemistry and Industry*, pp. 221–224 (Mar. 21, 1994).

*Primary Examiner*—Phyllis G. Spivack
*Attorney, Agent, or Firm*—James V. Harmon

[57] ABSTRACT

Methods are provided for treating schizophrenia, Tourette's Syndrome, obsessive-compulsive disorder, substance abuse or substance addiction including drug or alcohol addiction, manic-depression syndrome, anexoria or bulimia comprising administering an amount of cotinine or a pharmaceutically acceptable salt thereof, which amount is effective to reduce or alleviate at least one of the symptoms of schizophrenia, Tourette's Syndrome, obsessive-compulsive disorder, substance abuse or substance addiction including drug or alcohol addiction, manic-depression syndrome, anexoria or bulimia in a human or other mammal.

14 Claims, No Drawings

USE OF COTININE IN TREATING PSYCHIATRIC DISORDERS

This is a divisional application of Ser. No. 08/688,363 filed Jul. 30, 1996, now U.S. Pat No. 5,776,956.

FIELD OF THE INVENTION

This invention relates to treatment of certain psychiatric disorders through the administration of cotinine or salts of cotinine.

BACKGROUND OF THE INVENTION

U.S. Pat. No. 3,870,794 describes the use of cotinine in reducing anger, hostility, irritability and frustration, fear and anxiety without general sedation effects. U.S. Pat. No. 5,187,169 describes the effectiveness of cotinine in treating Alzheimer's Disease and Parkinson's disease through its ability to bind to and hence cause activation of nicotinic cholinergic receptors of the brain of the patient while acting as a nicotinic agonist. Australian Patent 273715 describes the use of cotinine as an effective tranquilizer through its action as a muscle relaxant or anti-spasmodic and in lowering blood pressure. Cotinine has also been shown to assist in tobacco withdrawal (pending U.S. application Ser. Nos. 124,004 and 885,314) as well as in human body weight management (pending U.S. application Ser. No. 964,277) and as a therapeutic agent in treating inflammatory bowel disorder such as Crohn's disease or ulcerative colitis in humans (pending U.S. application Ser. No. 08/405,607).

It has not, however, been previously recognized that cotinine is also able to provide a therapeutic effect in psychiatric disorders such as obsessive-compulsive behavior, Tourette's Syndrome and schizophrenia which are characterized by irrational behavior or repetitive thoughts. In obsessive-compulsive behavior, the patient is under a compulsion to repeat irrational or inappropriate behavior patterns and/or thoughts, while in Tourette's Syndrome the patient has an uncontrollable compulsion to utter inappropriate sounds or words. Similarly, in schizophrenia, the patient has uncontrolled inappropriate or irrational thoughts, delusions or behavior patterns. Schizophrenia, of course, has other characteristics, primarily disorganized or impoverished speech or behavior, flattened affect and avolition, social withdrawal and diminished interest in school or work. While a number of pharmacological treatments have been used for these psychiatric disorders in recent years with a degree of success, no studies have reported the successful treatment of all subjects or the absence of unwanted side effects, e.g., depression, drowsiness, sedation, tardive dyskinesia, agranulocytosis, and other problems. Consequently, a continuing need exists for pharmacological treatments that will alleviate or reduce obsessive-compulsive disorder, Tourette's Syndrome and schizophrenia.

These and other more detailed and specific objects of the present invention will be better understood by reference to the following detailed description which illustrates by way of example but a few of the various forms of the invention within the scope of the appended claims.

SUMMARY OF THE INVENTION

In accordance with the present invention, cotinine or the pharmaceutically acceptable salts thereof, such as the tartrate, aspartate, lactate, malate, citrate, fumarate, sulfate or chloride salts, are used in treating obsessive-compulsive behavior, Tourette's Syndrome, and schizophrenia. The present invention provides a therapeutic method of treatment to reduce or alleviate the symptoms of the aforesaid disorders. In a preferred embodiment, the present invention provides a therapeutic method to alleviate or reduce the symptoms of obsessive-compulsive disorder, Tourette's Syndrome and schizophrenia through the administration of any suitable dosage form, e.g., oral administration, injection, sublingual absorption, as a constituent of chewing gum to be chewed by the patient, as a transdermal patch to be applied to the skin of the patient, or through other suitable forms of administration.

The present invention also provides, as an article of manufacture, a packaging material such as a box, bottle, tube, spray or insufflator, intravenous bag, envelope or the like and at least one unit dosage form of a pharmaceutical agent contained in the package wherein the pharmaceutical agent comprises cotinine or a pharmaceutically acceptable salt thereof in an amount effective to alleviate or reduce the symptoms of obsessive-compulsive disorder, Tourette's Syndrome or schizophrenia, and wherein the package includes instructions indicating use for alleviating obsessive-compulsive disorder, Tourette's Syndrome or schizophrenia. Suitable instructions include printed labels, printed package inserts, tags, cassette tapes and the like.

DETAILED DESCRIPTION OF THE INVENTION

This invention provides a new and useful medicinal treatment used in alleviating or reducing the symptoms of obsessive-compulsive disorder, Tourette's Syndrome and schizophrenia in humans or other mammals. The treatment is effective in altering the emotional state of the human subject treated by the pharmaceutical agent. Both the behavior and emotional state, namely a compulsion by the patient to repeat thoughts or exhibit inappropriate or irrational behavior, are alleviated or reduced without unwanted side effects such as depression, drowsiness or sedation. In addition, the inappropriate behavior and/or irrational thoughts are reduced and supplanted by improved and more appropriate behavior and thought processes.

The treatment concerns the administration to a mammal, and especially a human being, in a pharmaceutically acceptable dosage form, a therapeutically effective amount of cotinine or its pharmacologically acceptable salts for alleviating or reducing the symptoms of obsessive-compulsive disorder, Tourette's Syndrome and schizophrenia.

It is known that after a person consumes nicotine, the nicotine is metabolized in four to six hours to produce cotinine. Cotinine begins to accumulate in the blood shortly after nicotine is consumed but, because of the toxicity of nicotine, cotinine is present in relatively low concentrations in the blood as the result of consuming nicotine. Nicotine has a half-life in the human of about one to two hours, whereas cotinine has a half-life of about 16 to 17 hours, and consequently is present in the blood much longer than nicotine. A one-pack-a-day smoker would usually have a nicotine blood concentration of about 20 ng/ml or about $\frac{1}{10}$ $\mu$mol/l to about 1 $\mu$mol/l, while a one-half-pack-a-day smoker will have a cotinine level of about 300 ng/ml or about 2 $\mu$mol/l. Because cotinine is virtually nontoxic, it can be present in the blood in relatively high amounts, say, 18,000 ng/ml without producing deleterious effects in humans. In accordance with the present invention, cotinine is used in amounts which produce much higher blood levels than that found in smokers.

Cotinine has been shown in U.S. Pat. No. 5,187,169 to pass the blood-brain barrier in the treatment of Alzheimer's and Parkinson's diseases, disorders that are correlated with a loss of cholinergic mediated neurotransmission. Because these diseases respond to cotinine, it is theorized that cotinine acts on cholinergic neurotransmission. There are, of course, many different types of cholinergic neuron receptors in mammals, and cotinine may express different affinity for and produce different effects on these various receptors.

There is also evidence that the weight control utility of cotinine, as well as the benefit in relieving muscle spasms and treating anger/hostility, result from cotinine's ability to modulate directly or indirectly other neurotransmitters such as serotonin, norepinephrine, dopamine or glutamate (U.S. Pat. No. 5,187,169).

While the effectiveness of cotinine for treating obsessive-compulsive disorder, Tourette's Syndrome and schizophrenia has never appeared in the literature, the relationship between nicotine and schizophrenia has been noted, e.g., through the recognition that almost all schizophrenics smoke incessantly, apparently in an attempt at self-medication [Freedman R., Hall M., Adler L. E., Leonard S. "Evidence in Postmortem Brain Tissue for Decreased Number of Hippocampal Nicotinic Receptors in Schizophrenia. *Biol. Psychiatry.* 38(1):22–33 (1995)]. It is also common to see many participants in Alcoholics Anonymous or Narcotics Anonymous groups smoking feverishly. Moreover, it has been recognized by the Hazelden Treatment Center at Center City, Minn., that continued smoking is considered to be important for a patient's success in his or her anti-addiction program. From these and other observations together with the discoveries reported hereinbelow, I find adequate evidence to conclude that these patients are trying to self-medicate their addictive or psychiatric disorders by consuming nicotine. In other words, the patients are reducing disease symptoms by consuming nicotine which is quickly metabolized to cotinine.

Nicotine has been shown to be effective in the treatment of Tourette's Syndrome [McConville B. J., Sanberg P. R., Fogelson M. H., King J., Cirino P., Parker K. W., Norman A. B. "The Effects of Nicotine Plus Haloperidol Compared to Nicotine Only and Placebo Nicotine Only in Reducing Tic Severity and Frequency in Tourette's Disorder." *Biol. Psychiatry.* 31(8):832–840 (1992)]. I have now found that data developed in the following Examples demonstrate that cotinine, by virtue of its low toxicity and longer half-life, is even more effective in treating Tourette's Syndrome than is the administration of nicotine.

The effectiveness of nicotine in treating other psychiatric conditions has been recognized in U.S. Pat. Nos. 5,187,169 and 5,298,257. Consequently, there is a clear relationship between nicotine and brain activity. The role of the central nervous system nicotinic receptors in human cognitive function and the involvement of the central nicotinic receptors in several degenerative brain disorders has been recognized by Paul Newhouse [Newhouse P. A., Potter A., Corwin J., Lenox R. "Age-related Effects of the Nicotinic Antagonist Mecamylamine on Cognition and Behavior. *Neuropsychopharmacology.* 10(2):93–107 (1994)]. The effectiveness of cotinine itself has already been demonstrated in alleviating tobacco addiction. See, pending U.S. patent application Ser. Nos. 885,314 and 124,004. The present invention is based in part on the finding described below in the examples that cotinine is the primary therapeutic agent for these and other actions typically ascribed to nicotine. I have found, however, that since cotinine in contrast to nicotine is very nontoxic in humans, it is possible to alleviate or reduce the symptoms of obsessive-compulsive disorder, Tourette's Syndrome and schizophrenia by providing massive doses of the drug as required to achieve therapeutic results so as to provide blood levels which cannot be tolerated with nicotine because of its toxicity.

Neuro-receptor binding site radioimmunoassay studies using human and other mammalian tissue described in the following examples with nicotine and cotinine demonstrate that cotinine at the same blood level is as effective or more effective than nicotine in many receptor sites. In addition, any curative effect produced by nicotine in obsessive-compulsive disorder, Tourette's Syndrome and schizophrenia can be achieved to a much greater degree with cotinine than with nicotine in accordance with the findings of the present invention. The effectiveness of cotinine, which will be described in greater detail below, is shown for example in human tissue neuro-receptor binding site studies to be about 19 times as effective in binding as an equal concentration of nicotine at the muscarinic-1 receptor and about five times as effective as an equal concentration of nicotine at the muscarinic-2 receptor when binding is expressed as percent inhibition of the receptor. Thus, for these human receptors, cotinine is many times more effective than nicotine at the same concentration in inhibiting the receptor binding activity of those receptors and can be administered in much greater amounts.

In producing its therapeutic effect, cotinine may be acting as a cholinergic agonist which is the effect usually attributed to nicotine. Thus, the cotinine acts essentially to slow down the over-activity of certain neural receptors, such as those that are receptors to dopamine, serotonin, acetylcholine, muscarine and the like. Cotinine's ability to alter neural communication mediated by the above neurotransmitters or the combination of them is the apparent reason for its utility in treating obsessive-compulsive disorder, Tourette's Syndrome and schizophrenia.

The exact psychoactive neuroleptic activity of cotinine is unknown. It is known, however, to have serotonergic activity. The present invention demonstrates several other actions of cotinine.

Tourette's Syndrome and Other Obsessive-Compulsive Disorders

Tourette's Syndrome is characterized by an autosomal dominant multiple tic disorder with variable penetrance progressing to multiple complex movements including respiratory and vocal tics, grunting, barking noises evolving into compulsive utterances. The neuroleptic drug of choice is haloperidol (Haldol™). Clonidine and pimozide are also used. Haloperidol is a strong tranquilizer that is believed to act by interfering the action of dopamine, thereby reducing anxiety and agitation and improving coherence. The effectiveness of nicotine in treating Tourette's Syndrome was described by B. J. McConville and P. R. Sanberg in *Biological Psychiatry,* 31(8):832–840 (1992). They demonstrated long-term effects of nicotine from relatively short term application of nicotine treatment with and without concurrent neuroleptic therapy. In contrast to the prior art, Tourette's Syndrome is treated in accordance with the present invention by the direct administration of an effective amount of cotinine or pharmacologically acceptable salts thereof for reducing or eliminating the symptoms of Tourette's Syndrome behavior. The Examples which follow below indicate that treatment with cotinine alleviates the compulsive speech behavior more effectively than nicotine. Besides being more effective than nicotine, cotinine lacks virtually any side effects as well as having a relatively long terminal elimination half-life of about 16 hours versus two hours for nicotine, and consequently acts in reducing the symptoms of Tourette's Syndrome over a longer period of time.

In two prior human studies, the pharmacokinetic profiles of intravenous and orally administered cotinine were examined without emphasis on measuring the subjective and/or physiological changes induced by this compound [N. L. Benowitz et al., *Clin. Pharm. and Ther.* 34:604 (1983). P. J. DeSchepper et al., *Eur. J. Pharmacol.* 31:583 (1987)]. Moreover, using an uncontrolled experimental design, Benowitz et al., *Clin. Pharm. and Ther.* 34:604 (1983), found that intravenous cotinine infusion over 60 minutes produced no cardiovascular changes and significant decreases in subjective ratings of desire to smoke, irritability, low energy and anxiety/tension. These changes were comparable to placebo-induced changes found in other experiments with nicotine. Using a rapid infusion of cotinine over 5 minutes, no significant changes in the subjective ratings were observed. Consequently, Benowitz and his colleagues concluded that cotinine lacked significant pharmacologic activity in humans. In spite of this, nicotine, the precursor of cotinine, has an established utility in treating Tourette's Syndrome [B. J. McConville, P. R. Sanberg. Ibid., p.8]. I have now discovered that the direct administration of cotinine will produce greater binding activity than nicotine at many sites and is therefore indicated to be more effective than nicotine in the treatment of Tourette's Syndrome and can also be used in much higher blood concentrations. The effectiveness is believed to be primarily due my finding that cotinine mimics or exceeds the blocking effect of nicotine at many neural receptor sites.

A brief review of neural activity will provide more complete understanding of the invention. An electrical impulse traveling along an excited neuron will trigger the release of neurotransmitters from the excited cell into the synaptic junction at the end of the neuron, causing the next cell to take in or exude selected ions, e.g., calcium and sodium. By altering the flow of charges across the membrane of the second cell, the neurotransmitter chemical, e.g., acetylcholine, can give rise to a new impulse. It is well known that nicotine couples with a part of the receptor molecule at the synapse designed to bind to the neurotransmitter acetylcholine. The nicotine thus bound to the receptor serves as an acetylcholine agonist mimicking the stimulatory effect of the naturally produced acetylcholine. It is now known that the nicotine-sensitive or nicotinic acetylcholine receptors in the synaptic junction are present in the central nervous system of all higher vertebrates. The brain has many other receptors, including a class of receptors known as muscarinic receptors as well as numerous others which were tested in the examples that follow. Nicotine, however, has a blocking effect for other receptors in addition to the nicotinic-acetylcholine receptors, and it is the nicotinic-acetylcholine receptors, as well as others, that are active in the chain of events that leads to what is known as Tourette's Syndrome, a disorder which has previously been at least partially corrected by the administration of nicotine. Sanberg (Ibid., p.8) has shown the effectiveness of treating Tourette's Syndrome with psychoactive (neuroleptic) agents such as Haldol™ which blocks dopamine receptors. He showed that nicotine makes Haldol™ more effective. He showed that nicotine with Haldol™ works even better than Haldol™ alone, and that nicotine alone appears to be effective in treating Tourette's Syndrome. Moreover, it was demonstrated that the skin patches containing nicotine had a lasting benefit for weeks to months. The blocking effect of nicotine that was found at the receptor sites is believed to be the same mechanism through which cotinine is effective in treating Tourette's Syndrome. While the effectiveness of the present invention is not known with certainty, it is speculated that new receptors synthesized by the body after exposure to cotinine may act essentially to cure the defect which causes Tourette's Syndrome. An example of this is the likelihood that tyrosine hydroxylase activity is induced by cotinine at the receptor site.

Obsessive-Compulsive Disorder

Obsessive-compulsive disorder (OCD) is characterized by the presence of recurrent ideas and fantasies and repetitive impulses or actions that the patient recognizes as morbid and toward which he feels a strong inner resistance. Some research suggests that disturbances in the function of the basal ganglia, especially in the seratonin receptors may be an important element in OCD. One established treatment of choice is the administration of the neuroleptic drug clomipramine (Anafranil™). Research has indicated that clomipramine increases brain tissue concentrations of certain nerve impulse transmitters, especially seratonin, by blocking seratonin re-uptake. Nicotine acts as an agonist at the neurotransmitter receptor site much in the same way as the drug clomipramine. Thus, clomipramine mimics the stimulatory effect of the naturally produced acetylcholine so as to become bound to other receptor sites as well, and cotinine apparently acts in a similar manner as revealed in the examples below to thereby alleviate or control obsessive-compulsive behavior.

Schizophrenia

Schizophrenia is a disabling psychiatric disorder characterized by delusions, hallucinations, disorganized or impoverished speech, obsessive or compulsive behavior, flattened affect, and avolition. The treatment of schizophrenia with drugs has been heavily influenced by the hypothesis that certain dopamine pathways are overactive [Seeman P., Niznik H. B. "Dopamine Receptors and Transporters in Parkinson's Disease and Schizophrenia." *FASEB J* 4:2737–44 (1990)]. Evidence for dopamine over-activity in patients with schizophrenia includes the capacity of anti-psychotic drugs to block dopamine receptors in vivo and in vitro [Creese I., Burt D. R., Schneider S. H. "Dopamine Receptor Binding Predicts Clinical and Pharmacological Potencies of Anti-schizophrenic Drugs." *Science*. 192:481–3 (1976)]. In addition, clinical efficacy of anti-psychotic drugs is, in general, highly correlated with their ability to block dopamine $D_2$ receptors [Seeman P., Lee T., Chau-Wong M., Wong K. "Anti-psychotic Drug Doses and Neuroleptic/Dopamine Receptors." *Nature*. 261:717–9 (1976)]. Moreover, dopamine agonists exacerbate the symptoms and signs of schizophrenia. Other receptors may also be involved in the therapeutic or adverse effects of specific drugs; however, all effective anti-psychotic drugs block some type of dopamine receptor [Seeman P. "Dopamine Receptor Sequences: Therapeutic Levels of Neuroleptics Occupy D9 Receptors, Clozapine Occupies D4." *Neuropsychopharmacology*, 7:261–84 (1992)]. One of the drugs, clozapine, that is highly effective in treating schizophrenia has a relatively high affinity for dopamine D1 and D4, 5-$HT_2$ muscarine in alpha-adrenergic receptors and is also a dopamine D2 receptor antagonist [Seeman P., Niznik, H. B. "Dopamine Receptors and Transporters in Parkinson's Disease and Schizophrenia." *FASEB J.*, 4:2737–44 (1990); Seeman P. "Dopamine Receptor Sequences: Therapeutic Levels of Neuroleptics Occupy D2 Receptors, Clozapine Occupies D4." *Neuropsychopharmacology*. 7:261–84 (1992)].

Research conducted by Edward Levin at Duke University shows that a side effect resulting from haloperidol therapy in treating schizophrenia could be reduced or blunted with nicotine which, as explained above, is quickly converted to cotinine in the body. Cotinine is therefore indicated to be of value in enhancing haloperidol therapy in the treatment of schizophrenia. The effect of cotinine on glutamic acid decarboxylase (GAD) described below should play an important role in enhancing haloperidol therapy in schizophrenia.

The in vitro tests using human and animal tissue that were conducted in developing the present invention show that cotinine has the same high affinity for many of the same receptor sites as clozapine. Consequently, its action and effectiveness in schizophrenia is believed to be of a similar origin.

Freedman has shown nicotine to be effective in normalizing the psychophysiological defects of schizophrenia. It is well known that schizophrenics are heavy smokers. This finding supports an explanation for the consumption of nicotine by these patients as a self-administered therapy. Cholinergic neurons may be involved in schizophrenia. It has been shown that bungarotoxin-sensitive cholinergic receptors in the hippocampus are involved in duplicating a second sonic response characteristic of schizophrenia. Nicotine appears to be effective in inhibiting typical schizophrenic activity when used in combination with mecamylamine (MEC). The use of nicotine is not, however, acceptable as a therapy for schizophrenia because a high dose of nicotine (which can be toxic) is needed and the effect is short-lived. Thus, tachyphylaxis occurs in short order [Freedman R., Hall M., Adler L. E., Leonard S. "Evidence in Postmortem Brain Tissue for Decreased Number of Hippocampal Nicotinic Receptors in Schizophrenia. Biol. Psychiatry. 38(1):22–33 (1995)].

In tests described below conducted in the development of the present invention, cotinine was found to have greater receptor binding activity than nicotine at the same concentration at many of the same receptor sites examined and can also be administered to humans at a much higher concentration. In contrast to nicotine, cotinine can be used at a much higher blood level and, due to its greater half-life, is effective for about eight times as long as nicotine. In addition, I have found that cotinine has greater activity than nicotine at many of the same receptor sites that bind nicotine which further facilitates its effectiveness.

Cotinine Dosage Forms

Cotinine (1-methyl-5-(3-pyridinyl)-2-pyrrolidionone) has the formula shown below:

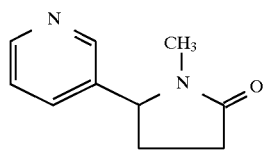

The physiologically active form is the (−)-isomer, so as used herein, the term "cotinine" includes (−)-cotinine, or the racemic form, (±)-cotinine. The free base, depicted above, can be employed in the practice of the invention, as can the pharmaceutically acceptable salts. These include the amine-acid addition salts of nontoxic organic acids or inorganic acids, such as the tartarate, fumarate ("scotine"), citrate, maleate, malate, hydrobromide, hydrochloride, sulfate, phosphate and the like. For example, see F. Vaitekunas, *J. Amer. Chem. Soc.* 79:149 (1957). E. R. Bowman et al. in *J. Pharmacol. and Fxp. Ther.* 135:306 (1962) report the preparation of (−)-cotinine free base from (−)-nicotine. The preparation and purification of (−)-cotinine fumarate is described by N. L. Benowitz et al., *Clin. Pharmacol. Ther.* 34:604 (1983).

Cotinine is the major metabolite of nicotine which accumulates in the body as a result of nicotine exposure and has previously been believed to be pharmacologically inactive. For example, see N. L. Benowitz, "The Use of Biologic Fluid Samples in Assessing Tobacco Smoke Consumption", in *Measurement in the Analysis and Treatment of Smoking Behavior*, J. Grabowski et al., eds., *NIDA Research Monograph No. 48*, *U.S. DHHS, PHS, ADAMHA* (1983). In contrast to nicotine, cotinine has a relatively long terminal elimination half-life (two versus sixteen hours, respectively). Due to this pharmacological characteristic, cotinine has become the principally used objective biochemical marker of nicotine exposure in cigarette smoking and/or cessation-related research paradigms.

While cotinine is a well-known metabolite of nicotine and is routinely measured in many laboratories, no systematic investigation of the physiological and subjective effects produced by intravenous cotinine administration has been performed in humans. K. I. Yamamoto, et al., *International J. Neuropharmacol.* 4:359 (1965) reported that intravenous cotinine produced increases only slightly in EEG activity and behavioral arousal in cats with only a slight decrease in blood pressure. In squirrel monkeys, intramuscular cotinine injections increased rates of responding on fixed interval schedules of reinforcement over a wide range of doses [M. E. Risner et al., *J. Pharmacol. and Exp. Ther.* 234:113 (1985); S. R. Goldberg et al., *Psychopharmacology.* 97:295 (1989)]. These findings, taken together, suggest that cotinine is behaviorally active. However, the pharmacologic mechanism of action has yet to be determined.

In two recent human studies, the pharmacokinetic profiles of intravenous and orally administered cotinine were examined without emphasis on measuring the subjective and/or physiological changes induced by this compound [N. L. Benowitz et al., *Clin. Pharmacol. and Ther.* 34:604 (1983); P. J. DeSchepper et al., *Eur. J Pharmacol.* 31:583 (1987)]. Moreover, using an uncontrolled experimental design, Benowitz et al., *Clin. Pharmacol. and Ther.* 34:604 (1983), found that intravenous cotinine infusion over 60 minutes produced no cardiovascular changes and significant decreases in subjective ratings of desire to smoke, irritability, low energy and anxiety/tension. These changes were comparable to placebo-induced changes found in other experiments with nicotine. Using a rapid infusion of cotinine over 5 minutes, no significant changes in the subjective ratings were observed. Consequently, Benowitz and his colleagues concluded that cotinine lacked significant pharmacologic activity in humans.

Administration and Dosages

While it is possible that, for use in therapy, cotinine and/or its salts may be administered as the pure chemicals, as by inhalation of a fine powder via an insufflator, it is preferable to present the active ingredient as a pharmaceutical formulation. The invention thus further provides a pharmaceutical formulation comprising cotinine and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented in discrete unit dosage forms such as hard or soft gelatin capsules, cachets or tablets each containing a predetermined amount of the active ingredient; as a powder or as granules; as a solution, a suspension or as an emulsion; in a chewable base such as a synthetic resin or chicle for ingestion of the cotinine from chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the present invention may also be formulated for parenteral administration (e.g., by injection, for example, bolus injection or continuous infusion) and may be presented in unit dosage forms in ampules, pre-filled syringes, small volume infusion containers or multi-dose containers with an added preservative. The compositions may take such forms as suspensions, solutions, or emulsions in oily or aqueous vehicles, and may contain formulatory agents such as suspending, stabilizing and/or dispersing agents. Alternatively the active ingredient may be in powder form, obtained by aseptic isolation of sterile solid or by lyophilization from solution, for constitution with a suitable vehicle, e.g., sterile, pyrogen-free water, before use.

For topical administration to the epidermis, the cotinine may be formulated as ointments, creams or lotions, or as the active ingredient of a transdermal patch. Suitable transdermal delivery systems are disclosed, for example, in A. Fisher et al. (U.S. Pat. No. 4,788,603) or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122; 4,383,529; or 4,051,842.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an inhaler such as an insufflator, nebulizer or a pressurized pack or other convenient means of delivering an aerosol spray, smoke, vapor, mist or powder. Pressurized packs may comprise a suitable propellant such as dichlorodifluoromethane, trichlorofluoromethane, dichlorotetrafluoromethane, carbon dioxide or other suitable gas. In the case of a pressurized aerosol, the dosage unit may be determined by providing a valve to deliver a metered amount.

Alternatively, for administration by inhalation or insufflation, the compounds according to the present invention may take the form of a dry powder composition, for example, a powder mix of the compound and a suitable powder base such as lactose or starch. The powder combination may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the cotinine can be administered as drops, gels (see, S. Chrai et al., U.S. Pat. No. 4,255,415), gums (see, S. L. Lin et al., U.S. Pat. No. 4,136,177) or via a prolonged-release ocular insert (see, A. S. Michaels, U.S. Pat. No. 3,867,519 and H. M. Haddad et al., U.S. Pat. No. 3,870,791).

The pharmaceutical compositions according to the invention may also contain other adjuvants such as flavorings, colorings, antimicrobial agents, or preservatives.

It will be further appreciated that the amount of cotinine, or an active salt or derivative thereof, required for use in treatment will vary not only with the particular salt selected but also with the route of administration, the nature of the condition being treated, and the age and condition of the patient and will be ultimately at the discretion of the attendant physician or clinician.

In general, however, a suitable dose will be in the range of from about 0.5 mg/kg to about 100 mg/kg, e.g, from about 3 mg/kg to about 75 mg/kg of body weight per day, such as 5 mg to about 50 mg per kilogram of body weight of the recipient per day, preferably in the range of 5 mg/kg/day to 90 mg/kg/day, most preferably in the range of 6 mg/kg/day to 60 mg/kg/day, calculated as (−)-cotinine in the free base form.

The compound is conveniently administered in unit dosage form; for example, containing 5 mg to 1000 mg, conveniently 10 mg to 750 mg, most conveniently, 40–50 mg to 100–500 mg of active ingredient per unit dosage form.

Ideally, the active ingredient should be administered to achieve peak plasma concentrations of the active compound of from about 0.5 $\mu$M, preferably about 1 $\mu$M to 50 $\mu$M, most preferably about 2 $\mu$M to about 30 $\mu$M. This may be achieved, for example, by the intravenous injection of a 0.5% to 50% solution of the active ingredient, optionally in saline, or orally administered as a bolus containing about 1–100 mg, preferably about 25–95 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The preferred dose of the compound is that amount that is effective to treat the psychiatric disorder from which the patient is suffering. The term "effective amount" or "effective dose" means that amount sufficient to pass across the blood-brain barrier so as to bind to relevant receptor sites in the central nervous system of the patient and to elicit neuropharmacological effects, e.g., by modifying neurotransmitter activity so as to be effective in treating the disease by decreasing the symptoms of the particular psychiatric disorder being treated.

Cotinine has a long in vivo half-life of about 16 to 17 hours, complete oral bioavailability, minimal effect on the cardiovascular system, and has not been reported to be harmful even at very high doses in many species, including man. Also, because cotinine has no significant effect on the heart, it can be used in much higher concentrations than nicotine.

The invention will be further described by reference to the following examples.

EXAMPLES

Tissue cultures were prepared using standard laboratory practice for the following tissues: human recombinant $M_1$ clone, human recombinant $M_2$ clone, guinea pig striatal membranes, rat cortical membranes, rat striatal membranes, rat forebrain membranes, bovine hippocampal membranes, guinea pig cerebellar membranes, rat kidney membranes, recombinant rat $5HT_7$ clone, and rat cerebellar membranes. Radioimmunoassay studies were conducted to determine the binding activity of nicotine, cotinine and cotinine fumarate as described in the literature references listed in the examples for the sites, neurotransmitters and receptors indicated.

Example 1

Dopamine Reuptake Binding Assay

| Reference Compounds Ki(nM) Assay Characteristics | Bupropion | | 935.0 | |
|---|---|---|---|---|
| $K_d$ (binding affinity): | 28.0 nM | | | |
| $B_{max}$ (receptor number): | 113 fmol/mg tissue (wet weight) | | | |
| Degree of Specific Binding: | 70–80% (Non-specific binding determine using $10^{-4}$ M bupropion) | | | |
| Materials and Methods: | | | | |
| Receptor Source: | Guinea pig striatal membranes | | | |
| Radioligand: | [$^3$H]WIN,35,428 (60–87 Ci/mmol) | | | |
| | Final ligand concentration - [1.0 nM] | | | |
| Reference Compound: | Bupropion | | | |
| Positive Control: | Bupropion | | | |
| Incubation Conditions: | Reactions are carried out in 50 nM TRIS-HCl (pH 7.4) containing 100 nM NaCl 25° C. for 2 hours. The reaction is terminated by rapid vacuum filtration onto glass fiber filters. Radioactivity trapped onto the filters is determined and compared to control values in order to ascertain any interactions of test compound with the dopamine uptake site. | | | |
| | Literature references to receptor binding activity procedure: | | | |
| | Madras, et al. Cocaine Receptors Labeled by [$^3$H]2Beta-Carbomethoxy-3-Beta-(4-Fluorophenyl)topane. Mol. Pharmacol. 36: 518–524 (1989) with modifications. | | | |
| | Javitch, J. J., Blaustein, R. O., and Snyder, S. H. [$^3$H]Mazindol Binding Associated with Neuronal Dopamine and Norepinephrine Uptake Sites. Mol. Pharmacol. 26: 35–44 (1984). | | | |
| Results: | Receptor Binding Activity Percent Inhibition Average (N = 2) | | | |
| | Nicotine $10^{-6}$M | Cotinine $10^{-4}$M | Cotinine $10^{-6}$M | Cotinine$_2$ Fumarate $10^{-6}$M |
| | 9.2% | 7.5% | 14.2% | 4.6% |

Example 2

Gamma-Aminobutyric Acid (GABA) Uptake Binding Assay

| Reference Compounds Ki(nM) | Nipecotic Acid | 37,000 |
|---|---|---|
|  | GABA | 26,000 |

Assay Characteristics

| | |
|---|---|
| $K_d$ (binding affinity): | 18,000 nM |
| $B_{max}$ (receptor number): | 780 fmol/mg tissue (wet weight) |
| Degree of Specific Binding: | 90% (Non-specific binding determine using 1 nM Nipecotic Acid) |
| Materials and Methods: | |
| Receptor Source: | Rat cortical membranes |
| Radioligand: | [$^3$H]GABA (70–80 Ci/mmol) |
|  | Final ligand concentration - [3.6 nM] |
| Reference Compound: | Nipecotic acid |
| Positive Control: | Nipecotic acid |
| Incubation Conditions: | Reactions are carried out in KREBS-HEPES (pH 7.4) buffer at 37° C. for 3 minutes. The reaction is terminated by rapid vacuum filtration onto glass fiber filters. Radioactivity trapped onto the filters is determined and compared to control values in order to ascertain any interactions of test compound with the GABA uptake site. |
|  | Literature references to receptor binding activity procedure: |
|  | Karbon, E. W., Enna, S. J., and Ferkany, J. W. Biochemical and Behavioral Studies Following Subchronic Administration of GABA Uptake Inhibitors in Mice. Neuropharmacology. 30: 1198–1192 (1991). |
|  | Falch, E., Hedegaard, A., et al. Comparative Stereostructure - Activity Studies on $GABA_A$ and $GABA_B$ Receptor Sites and GABA Uptake using Rat Brain Membranes. Jrnl. Neurochem. 47(3): 898–903 (1986). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 12.1% | 7.4% | 13.9% | 15.8% |

Example 3

Nicotinic (Neuronal) Binding Assay

| Reference Compounds Ki(nM) | Nicotine Sulfate | 1.7 |
|---|---|---|
|  | Hexamethonium | >10,000 |
|  | Atropine | >10,000 |
|  | Tubocurarine | >10,000 |

Assay Characteristics

| | |
|---|---|
| $K_d$ (binding affinity): | 2.7 nM |
| $B_{max}$ (receptor number): | 118.4 fmol/mg protein |
| Degree of Specific Binding: | 80% (Non-specific binding determine using 0.2 μM nicotine sulfate) |
| Materials and Methods: | |
| Receptor Source: | Rat cortical membranes |
| Radioligand: | [$^3$H]N-methylcarbamylcholine iodide (70–87 Ci/mmol) |
|  | Final ligand concentration - [2.5 nM] |
| Reference Compound: | Nicotine sulfate |
| Positive Control: | Nicotine sulfate |
| Incubation Conditions: | Reactions are carried out in 50 mM TRIS-HCl (pH 7.4) containing 120 mM NaCl, 5.0 mM Kcl, 2.0 mM $CaCl_2$, 1.0 mM $MgCl_2$ and 3.0 μM atropine sulfate at 4° C. for 60 minutes. The reaction is terminated by rapid vacuum filtration onto glass fiber filters Radioactivity trapped onto the filters is determined and compared to control values in order to ascertain any interactions of test compound with the nicotinic binding site. |
|  | Literature references to receptor binding activity procedure: |
|  | Boska, P. and Quirion, R. [$^3$H]N-Methyl-Carbamylcholine: A New Radioligand Specific for Nicotinic Acetylcholine Receptors in the Brain. Eur. Jrnl. Pharmacol. 139: 323–333 (1987) with modifications. |
|  | Leutje, C. W., Patrick, J., and Seguela, P. Nicotine Receptors in the Mammalian Brain. FASEB Jrnl. 4: 2753–2760 (1990). |

-continued

| Results: | Receptor Binding Activity Percent Inhibition Average (N = 2) | | | |
|---|---|---|---|---|
| | Nicotine $10^{-6}$M | Cotinine $10^{-4}$M | Cotinine $10^{-6}$M | Cotinine$_2$ Fumarate $10^{-6}$M |
| | 98.5% | 12.0% | 78.5% | 15.9% |

Example 4

Dopamine ($D_1$ Central) Binding Assay

| Reference Compounds Ki(nM) | SCH 23390 | 4.6 |
|---|---|---|
| | Butaclamol | 37.3 |
| | Metoclopramide | 97.3 |
| | SKF 38393 | 127.0 |
| | Spiperone | 843.0 |
| Assay Characteristics | | |
| $K_d$ (binding affinity): | 5.3 nM | |
| $B_{max}$ (receptor number): | 69 fmol/mg tissue (wet weight) | |
| Degree of Specific Binding: | 90% (Non-specific binding determined using 1.0 $\mu$M SCH 23390) | |
| Materials and Methods: | | |
| Receptor Source: | Rat striatal membranes | |
| Radioligand: | [$^3$H]SCH 23390 (70–87 Ci/mmol) | |
| | Final ligand concentration - [0.5 nM] | |
| Reference Compound: | SCH 23390 | |
| Positive Control: | SCH 23390 | |
| Incubation Conditions: | Reactions are carried out in 50 mM HEPES (pH 7.4) containing 1.0 mM EDTA, 4.0 mM MgSO$_4$, and 10 $\mu$M ketanserin at 37° C. for 60 minutes. The reaction is terminated by rapid vacuum filtration onto glass fiber filters. Radioactivity trapped onto the filters is determined and compared to control values in order to ascertain any interactions of test compound with the dopamine binding site. Literature references to receptor binding activity procedure: Billard, W., Ruperto, V., Crosby, G., et al. Characterization of the Binding of [$^3$H}SCH 23390: A Selective $D_1$ Receptor Antagonist Ligand in Rat Striatum. Life Sciences. 35: 1885–1893 (1984) with modifications. Anderson, P. H., Gronvald, F. C., et al. NNC-112, NNC-687, and NNC-756, New Selective and Highly Potent Dopamine $D_1$ Receptor Antagonists. Eur. Jrnl. Pharma. 219(1): 45–52 (1992). | |

| Results: | Receptor Binding Activity Percent Inhibition Average (N = 2) | | | |
|---|---|---|---|---|
| | Nicotine $10^{-6}$M | Cotinine $10^{-4}$M | Cotinine $10^{-6}$M | Cotinine$_2$ Fumarate $10^{-6}$M |
| | 2.6% | 3.3% | 2.9% | -1.2% |

Example 5

Histamine ($H_2$) Binding Assay

| Reference Compounds Ki(nM) | Cimetidine | 650 |
|---|---|---|
| Assay Characteristics | | |
| $K_d$ (binding affinity): | 9.4 $\mu$M | |
| $B_{max}$ (receptor number): | 212 fmol/mg protein | |
| Degree of Specific Binding: | 60% (Non-specific binding determined using 10 mM cimetidine) | |
| Materials and Methods: | | |
| Receptor Source: | Guinea pig striatal membranes | |
| Radioligand: | [$^3$H]Tiotidine (70–90 Ci/mmol) | |
| | Final ligand concentration - [4.0 nM] | |
| Reference Compound: | Cimetidine | |
| Positive Control: | Cimetidine | |
| Incubation Conditions: | Reactions are carried out in 50 mM Na-KPO$_4$ (pH 7.4) at 25° C. for 20 minutes. The reaction is terminated by rapid vacuum filtration onto glass fiber filters. Radioactivity trapped onto the filters is determined and compared to control values in order to ascertain any interactions of test compound with the histamine$_2$ binding site. Literature references to receptor binding activity procedure: Gajtkowski, et al. Specific Binding of [$^3$H]Tiotidine to Histamine H$_2$ | |

| | |
|---|---|
| | -continued |
| | Receptors in Guinea Pig Cerebral Cortex. Nature. 304: 65–67 (1983) with modifications.<br>Martinez-Mur, M. I., Pollard, H., Moreau, J., et al. Three Histamine Receptors ($H_1$, $H_2$, and $H_3$) Visualized in the Brain of Human and Non-Human Primates. Brain Res. 526: 322–327 (1990).<br>Haaksma, E. E. J., Leurs, R., and Timmerman, H. Histamine Receptors: Subclasses and Specific Ligands. Pharmac. Ther. 47: 73–104 (1990). |
| Results: | Receptor Binding Activity Percent Inhibition Average (N = 2) |

| Nicotine<br>$10^{-6}$M | Cotinine<br>$10^{-4}$M | Cotinine<br>$10^{-6}$M | Cotinine$_2$ Fumarate<br>$10^{-8}$M |
|---|---|---|---|
| 45.9% | −1.4% | 9.2% | 14.7% |

Example 6

Histamine ($H_3$) Binding Assay

| | | |
|---|---|---|
| Reference Compounds Ki(nM) | R(-)-α-Methylhistamine | 0.79 |
| | Histamine | 59.3 |
| Assay Characteristics | | |
| $K_d$ (binding affinity): | 0.37 nM | |
| $B_{max}$ (receptor number): | 73 fmol/mg protein | |
| Degree of Specific Binding: | 90% (Non-specific binding determined using 1.0 μM R(-)α-Methylhistamine | |
| Materials and Methods: | | |
| Receptor Source: | Rat forebrain membranes | |
| Radioligand: | [$^3$H]$N^a$-methylhistamine (84.1 Ci/mmol)<br>Final ligand concentration - [0.2 nM] | |
| Reference Compound: | R(-)-α-Methylhistamine | |
| Positive Control: | R(-)-α-Methylhistamine | |
| Incubation Conditions: | Reactions are carried out in 50 mM TRIS-HCl (pH 7.5) for 40 minutes at 25° C. The reaction is terminated by rapid vacuum filtration onto glass fiber filters. Radioactivity trapped onto the filters is determined and compared to control values in order to ascertain any interactions of test compound with the histamine$_3$ binding site.<br>Literature references to receptor binding activity procedure:<br>West, Robert E., et al. Identification of Two $H_3$-Histamine Receptor Subtypes. Mol. Pharmacol. 38: 610–613 (1990) with modifications.<br>Arrang, J. M., Garbarg, M., Lancelot, J. C., et al. Highly Potent and Selective Ligands for Histamine $H_3$ Receptors. Nature. 327: 117–123 (1987) with modifications. | |
| Results: | Receptor Binding Activity Percent Inhibition Average (N = 2) | |

| Nicotine<br>$10^{-6}$M | Cotinine<br>$10^{-4}$M | Cotinine<br>$10^{-6}$M | Cotinine$_2$ Fumarate<br>$10^{-6}$M |
|---|---|---|---|
| 13.5% | 15.7% | 11.9% | 15.4% |

Example 7

Serotonin (5HT$_1$) Binding Assay

| | | |
|---|---|---|
| Reference Compounds Ki(nM) | 5-Carboxytryptamine (5-CT) | 2.2 |
| | 5-Hydroxytryptamine (5-HT) | 7.2 |
| | 5-Methoxytryptamine | 45.8 |
| | Methysergide | 790.0 |
| | CGS-12066B | 1,055.0 |
| Assay Characteristics | | |
| $K_d$ (binding affinity): | 2.8 nM | |
| $B_{max}$ (receptor number): | 9.2 fmol/mg protein | |
| Degree of Specific Binding: | 60% (Non-specific binding determined using 100 μM serotonin) | |
| Materials and Methods: | | |
| Receptor Source: | Rat cortical membranes | |
| Radioligand: | [$^3$H]Hydroxytryptamine binoxalate (15–30 Ci/mmol)<br>Final ligand concentration - [3.0 nM] | |
| Reference Compound: | Serotonin | |

-continued

| Positive Control: | Serotonin |
|---|---|
| Incubation Conditions: | Reactions are carried out in 50 mM TRIS-HCl (pH 7.4) at 37° C. for 45 minutes. The reaction is terminated by rapid vacuum filtration onto glass fiber filters. Radioactivity trapped onto the filters is determined and compared to control values in order to ascertain any interactions of test compound with the $5HT_1$ binding site. Literature references to receptor binding activity procedure: Peroutka, S. J., Snyder, S. H. Multiple Serotonin Receptors: Differential Binding of [$^3$H]-5-HT, [$^3$H]-LSD and [$^3$H]-Spiroperidol. Mol. Pharmacol. 16: 687–699 (1979) with modifications. Peroutka, S. J. and Snyder, S. H. Two Distinct Serotonin Receptors: Regional Variations in Receptor Binding in Mammalian Brain. Brain Research. 208: 339–347 (1981). Martin, G. R. and Humphrey, P. P. A. Classification Review for 5-HT: Current Perspectives on Classification and Nomenclature. Neuropharmacol. 3(3/4): 261–273 (1994). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| −1.4% | −0.8% | 10.9% | 5.4% |

Example 8

Serotonin ($5HT_{1A}$) Binding Assay

| Reference Compounds Ki(nM) | 8-OH-DPAT | 3.6 |
|---|---|---|
| | RU 24969 | 10.0 |
| | Serotonin | 12.4 |
| | Ketanserin | >10,000 |

| Assay Characteristics | |
|---|---|
| $K_d$ (binding affinity): | 2.0 nM |
| $B_{max}$ (receptor number): | 1.626 pmol/mg protein |
| Degree of Specific Binding: | 90% (Non-specific binding determined using 10 μM serotonin) |
| Materials and Methods: | |
| Receptor Source: | Bovine hippocampal membranes |
| Radioligand: | [$^3$H]-8-OH-DPAT (100 Ci/mmol) |
| | Final ligand concentration - [1.0 nM] |
| Reference Compound: | 8-OH-DPAT |
| Positive Control: | 8-OH-DPAT |
| Incubation Conditions: | Reactions are carried out in 50 mM TRIS-HCl (pH 7.4) at 37° C. for 10 minutes. The reaction is terminated by rapid vacuum filtration onto glass fiber filters. Radioactivity trapped onto the filters is determined and compared to control values in order to ascertain any interactions of test compound with the $5HT_{1A}$ binding site. Literature references to receptor binding activity procedure: Hoyer, D., Engel, G., et al. Molecular Pharmacology of $5HT_1$ and 5-HT$_2$ Recognition Sites in Rat and Pig Brain Membranes: Radioligand Binding Studies with [$^3$H]-5HT, [$^3$H]8-OH-DPAT, [$^{125}$I]-Iodocyanopindolol, [$^3$H]-Mesulergine and [$^3$H]-Ketanserin. Eur. Jrnl. Pharmacol. 118: 13–23 (1985) with modifications. Schoeffter, P. and Hoyer, D. How Selective is GR 43175? Interactions with Functional 5-HT$_{1A}$, 5-HT$_{1B}$, 5-HT$_{1C}$, and 5-HT$_{1D}$ Receptors. Naunyn-Schmiedeberg's Arch. Pharmac. 340: 135–138 (1989) with modifications. |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 3.3% | 1.4% | 1.1% | 2.7% |

Example 9

Serotonin (Non-Selective) Binding Assay

| Reference Compounds Ki(nM) | Methysergide | 5.7 |
|---|---|---|
| | Spiroperidol | 18.0 |
| | Mianserin | 33.0 |
| | 5-Methoxytryptamine | 210.0 |

-continued

| Assay Characteristics | |
|---|---|
| $K_d$ (binding affinity): | 7.2 nM |
| $B_{max}$ (receptor number): | 23 fmol/mg tissue (wet weight) |
| Degree of Specific Binding: | 75% (Non-specific binding determined using 1.0 μM LSD) |
| Materials and Methods: | |
| Receptor Source: | Rat cortical membranes |
| Radioligand: | [$^3$H]Lysergic acid diethylamide (60–70 Ci/mmol) |
| | Final ligand concentration - [5.0 nM] |
| Reference Compound: | Methysergide |
| Positive Control: | Methysergide |
| Incubation Conditions: | Reactions are carried out in 50 mM TRIS-HCl (pH 7.4) containing 4 mM CaCl$_2$, 0.1 mM pargyline and 0.1% ascorbic acid at 37° C. for 15 minutes. The reaction is terminated by rapid vacuum filtration onto glass fiber filters. Radioactivity trapped onto the filters is determined and compared to control values in order to ascertain any interactions of test compound with the serotonin binding site. Literature references to receptor binding activity procedure: Peroutka, S. J., Snyder, S. H. Multiple Serotonin Receptors: Differential Binding of [$^3$H]-5-HT, [$^3$H]-LSD and [$^3$H]-Spiroperidol. Mol. Pharmacol. 16: 687–699 (1979) with modifications. Peroutka, S. J. and Snyder, S. H. Two Distinct Serotonin Receptors: Regional Variations in Receptor Binding in Mammalian Brain. Brain Research. 208: 339–347 (1981). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 6.3% | 12.1% | 4.6% | 4.1% |

Example 10

Opiate (Delta) Binding Assay

| Reference Compounds Ki(nM) | | |
|---|---|---|
| | Naloxone | 25.2 |
| | DADLE | 0.9 |
| | DPDPE | 1.6 |
| | Cyclazocine | 4.8 |
| | Nalbuphine | 124.0 |
| | Pentazocine | 140.0 |
| | DAMGO | 145.5 |

| Assay Characteristics | |
|---|---|
| $K_d$ (binding affinity): | 2.12 nM |
| $B_{max}$ (receptor number): | 1.03 fmol/mg tissue (wet weight) |
| Degree of Specific Binding: | 80% (Non-specific binding determined using 10 μM naloxone) |
| Materials and Methods: | |
| Receptor Source: | Rat forebrain membranes |
| Radioligand: | [$^3$H]Enkephaline [2-D penicillamine, 5-D penicillamine]-(DPDPE) (30–60 Ci/mmol) |
| Reference Compound: | Final ligand concentration - [1.0 nM] |
| Positive Control: | Naloxone |
| Incubation Conditions: | Naloxone |
| | Reactions are carried out in 50 mM TRIS-HCl (pH 74) at 25° C. for 90 minutes. The reaction is terminated by rapid vacuum filtration onto glass fiber filters. Radioactivity trapped onto the filters is determined and compared to control values in order to ascertain any interactions of test compound with the delta opiate binding site. Literature references to receptor binding activity procedure: Akiyama, K., Gee, K. W., Mosberg, K. W. Yamamura, H. I. Characterization of [$^3$H]DPDPE Binding to Delta Opiate Receptors in the Rat Brain and Neuroblastomaglioma Hybrid Cell Line (NG 108–115). Proc. Nat'l Acad. Sci. 82: 2543 (1985) with modifications. Sofuoglu, M., Portoghese, P. S., and Takemori, A. E. δ-Opioid Receptor Binding in Mouse Brain: Evidence for Heterogeneous Binding Sites. Eur. Jrnl. Pharm. 216: 273–277 (1992). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 10.1% | 10.0% | 8.3% | 17.6% |

Example 11

Benzodiazepine (Peripheral) Binding Assay

| Reference Compounds Ki(nM) | PK11195 | 28.8 |
| --- | --- | --- |
| | RO54864 | 34.0 |
| | Diazepam | 574.0 |

Assay Characteristics

| $K_d$ (binding affinity): | 9.8 nM |
| --- | --- |
| $B_{max}$ (receptor number): | 23.9 fmol/mg tissue (wet weight) |
| Degree of Specific Binding: | 90% (Non-specific binding determined using 10 $\mu$M PK11195) |
| Materials and Methods: | |
| | |
| Receptor Source: | Rat kidney membranes |
| Radioligand: | [$^3$H]PK11195 (60–90 Ci/mmol) |
| | Final ligand concentration - [1.0 nM] |
| Reference Compound: | PK11195 |
| Positive Control: | PK11195 |
| Incubation Conditions: | Reactions are carried out in 50 mM TRIS-HCl (pH 7.7) at 0–4° C. for 60 minutes. The reaction is terminated by rapid vacuum filtration onto glass fiber filters. Radioactivity trapped onto the filters is determined and compared to control values in order to ascertain any interactions of test compound with the benzodiazepine (peripheral) binding site. |
| | Literature references to receptor binding activity procedure: |
| | Skowronski, R., et al. Photoaffinity Labeling of Peripheral Type Benzodiazepine Receptors in Rat Kidney Mitochondria with [$^3$H]PK14105. Eur. Jrnl. Pharmac. 148: 187–193 (1988) with modifications. |
| | Raghavendra Roa, V. L., Audet, R., Therrien, G., et al. Tissue Specific Alterations of Binding Sites for Peripheral Type Benzodiazepine Receptor Ligand [$^3$H]PK11195 in Rats Following Potacaval Anastomosis. Digestive Diseases & Sciences. 39(5): 1055–1063 (1994). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
| --- | --- | --- | --- |
| 3.1% | 1.4% | 8.5% | 1.8% |

Example 12

Glycine (Strychnine Insensitive) Binding Assay

| Reference Compounds Ki(nM) | Glycine | 187.0 |
| --- | --- | --- |
| | D-Serine | 703.0 |
| | D-Alanine | 895.0 |
| | L-Serine | 25,000 |
| | $\beta$-Alanine | 900,000 |

Assay Characteristics

| $K_d$ (binding affinity): | 443 nM |
| --- | --- |
| $B_{max}$ (receptor number): | 1.72 pmol/mg protein |
| Degree of Specific Binding: | 90% (Non-specific binding determine using 1.0 mM glycine) |
| Materials and Methods: | |
| | |
| Receptor Source: | Rat cortical membranes |
| Radioligand: | [$^3$H]Glycine (70–80 Ci/mmol) |
| | Final ligand concentration - [10.0 nM] |
| Reference Compound: | Glycine |
| Positive Control: | Glycine |
| Incubation Conditions: | Reactions are carried out in 50 mM HEPES (pH 7.1) at 4° C. for 30 minutes. The reaction is terminated by rapid vacuum filtration onto glass fiber filters. Radioactivity trapped onto the filters is determined and compared to control values in order to ascertain any interactions of test compound with the glycine binding site. |
| | Literature references to receptor binding activity procedure: |
| | Snell, L. D., Morter, R. S., and Johnson, K. M. Structural Requirements for Activation of the Glycine Receptor that Modulates the N-methyl-D-aspartate Operated Channel. Eur. Jrnl. Pharmacol. 156: 105–110(1988). |
| | Monahan, J. B., Corpus, V. M., Hood, W. F., et al. Characterization of a [$^3$H]Glycine Recognition Site as a Modulatory Site of the |

-continued

|  | NMDA Receptor Complex. Jrnl. Neurochem. 53(2): 370–375 (1989). |
|---|---|
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 1.5% | −0.6% | 10.9% | −5.6% |

Example 13

Muscarinic—$M_1$ Clone Binding Assay

| Reference Compounds Ki(nM) | Methylscopolamine | 0.7 |
|---|---|---|
|  | 4-DAMP-Methiodide | 0.6 |
|  | p-F-Hexahydrodifenidol | 8.5 |
|  | 3-α-chloroimperialine | 15.3 |
|  | Pirezepine | 21.7 |
|  | Tropicamide | 54.9 |
|  | Methoctramine | 412.0 |

Assay Characteristics

| $K_d$ (binding affinity): | 0.17 nM |
|---|---|
| $B_{max}$ (receptor number): | 1,825 pmol/mg protein |
| Degree of Specific Binding: | 90% (Non-specific binding determine using 1.0 μM Methylscopolamine bromide) |

Materials and Methods:

| Receptor Source: | Human recombinant $M_1$ clone |
|---|---|
| Radioligand: | [$^3$H]Methylscopolamine (80–100 Ci/mmol) Final ligand concentration - [0.2 nM] |
| Reference Compound: | (-)-Scopolamine, Methyl-, bromide (Methylscopolamine bromide) |
| Positive Control: | (-)-Scopolamine, Methyl-, bromide (Methylscopolamine bromide) |
| Incubation Conditions: | Reactions are carried out in 50 mM TRIS-HCl (pH 7.4) containing 10 nM MgCl$_2$, 1 mM EDTA for 60 minutes at 25° C. The reaction is terminated by rapid vacuum filtration onto glass fiber filters. Radioactivity trapped onto the filters is determined and compared to control values in order to ascertain any interactions of test compound(s) with the cloned muscarinic - $M_1$ binding site. Literature references to receptor binding activity procedure: Wei, H. B., Roeske, W. R., et al. Pharmacological Characterization of a Novel Muscarinic Partial Agonist, YM796, in Transfected Cells Experssing the $M_1$ or $M_2$ Muscarinic Receptor Gene. Life Sciences. 50(5): 355–363 (1992). Dorje, R., Wess, J., et al. Antagonist Binding Profiles of Five Cloned Human Muscarinic Receptor Subtypes. Jrnl. Pharmacol. Exp. Ther. 256(2): 727–733 (1991). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 0.9% | 19.5% | 15.5% | 3.1% |

Example 14

Muscarinic—$M_2$ Clone Binding Assay

| Reference Compounds Ki(nM) | Methylscopolamine | 0.5 |
|---|---|---|
|  | 3-α-chloroimperialine | 0.7 |
|  | 4-DAMP-Methiodide | 10.1 |
|  | Tropicamide | 19.4 |
|  | Methoctramine | 58.8 |
|  | p-F-Hexahydrodifenidol | 123.0 |
|  | Pirezepine | 551.0 |

Assay Characteristics

| $K_d$ (binding affinity): | 0.142 nM |
|---|---|
| $B_{max}$ (receptor number): | 3,670 pmol/mg protein |
| Degree of Specific Binding: | 90% (Non-specific binding determine using 1.0 μM Methylscopolamine bromide) |

-continued

| Materials and Methods: | |
|---|---|
| Receptor Source: | Human recombinant $M_2$ clone |
| Radioligand: | [$^3$H] Methylscopolamine (80–100 Ci/mmol) |
| | Final ligand concentration - [0.2 nM] |
| Reference Compound: | (-)-Scopolamine, Methyl-, bromide (Methylscopolamine bromide) |
| Positive Control: | (-)-Scopolamine, Methyl-, bromide (Methylscopolamine bromide) |
| Incubation Conditions: | Reactions are carried out in 50 mM TRIS-HCl (pH 7.4) containing 10 nM $MgCl_2$, 1 mM EDTA for 60 minutes at 25° C. The reaction is terminated by rapid vacuum filtration onto glass fiber filters. Radioactivity trapped onto the filters is determined and compared to control values in order to ascertain any interactions of test compound(s) with the cloned muscarinic - $M_2$ binding site. Literature references to receptor binding activity procedure: Wei, H. B., Roeske, W. R., et al. Pharmacological Characterization of a Novel Muscarinic Partial Agonist, YM796, in Transfected Cells Experssing the $M_1$ or $M_2$ Muscarinic Receptor Gene. Life Sciences. 50(5): 355–363 (1992). Dorje, R., Wess, J., et al. Antagonist Binding Profiles of Five Cloned Human Muscarinic Receptor Subtypes. Jrnl. Pharmacol. Exp. Ther. 256(2): 727–733 (1991). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 4.4% | 21.6% | 22.3% | 20.7% |

Example 15

Serotonin—5HT$_7$ Clone Binding Assay

| Reference Compounds Ki(nM) | 5-CT | 0.6 |
|---|---|---|
| | Mesulergine | 3.9 |

| Assay Characteristics | |
|---|---|
| $K_d$ (binding affinity): | 3.2 nM |
| $B_{max}$ (receptor number): | 710 fmol/mg protein |
| Degree of Specific Binding: | 85% (Non-specific binding determine using 1.0 $\mu$M 5-carboxamidotryptamine, 5-CT) |

| Materials and Methods: | |
|---|---|
| Receptor Source: | recombinant Rat 5HT$_7$ Clone |
| Radioligand: | [$^3$H]LSD (60–80 Ci/mmol) |
| | Final ligand concentration - [2.0 nM] |
| Reference Compound: | 5-CT |
| Positive Control: | 5-CT |
| Incubation Conditions: | Reactions are carried out in 50 mM TRIS-HCl (pH 7.4) containing 10 mM $MgCl_2$, 1 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin - 5HT$_7$ binding site. Literature references to receptor binding activity procedure: Shen, Y., et al. Molecular Cloning and Expression of a 5-hydroxy-tryptamine$_7$ Serotonin Receptor Subtype. Jrnl. Biol. Chem. (268): 18200–18204 (1993). |
| Results: | Receptor Binding Activity Percent Inhibition Average (N = 2) |

| Nicotine $10^{-6}$M | Cotinine $10^{-4}$M | Cotinine $10^{-6}$M | Cotinine$_2$ Fumarate $10^{-6}$M |
|---|---|---|---|
| 8.0% | 6.4% | -0.3% | 1.4% |

Example 16

Inositol Triphosphate (IP$_3$) Binding Assay

| Reference Compounds Ki(nM) | IP$_3$ | 21 |
|---|---|---|
| | IP$_4$ | 672 |
| | IP$_5$ | 6,850 |
| | IP$_2$ | >10,000 |
| | IP$_1$ | >100,000 |

-continued

Assay Characteristics $K_d$ (binding affinity):     40.0 nM
$B_{max}$ (receptor number):     23 pmol/mg protein
Degree of Specific Binding:     85% (Non-specific binding determined using 1.0 μM myo-inositol 1,4,5-triphosphate)

Materials and Methods:

Receptor Source:     Rat cerebellar membranes
Radioligand:     [$^3$H]IP$_3$ (10–30 Ci/mmol)
    Final ligand concentration - [4.0 nM]
Reference Compound:     D-myo-inositol 1,4,5-triphosphate
Positive Control:     D-myo-inositol 1,4,5-triphosphate
Incubation Conditions:     Reactions are carried out in 50 mM TRIS-HCl (pH 8.3) containing 1 mM EDTA at 0° C. for 10 minutes. The reaction is terminated by rapid vacuum filtration onto glass fiber filters. Radioactivity trapped onto the filters is determined and compared to control values in order to ascertain any interactions of test compound with the inositol triphospate binding site.
    Literature references to receptor binding activity procedure:
    Worley, P., Baraban, J., Supattapone, S., Wilson, V., and Snyder, S. H. Characterization of Inositol Triphosphate Receptor Binding in Brain. Jrnl. Biochem. 262(25): 12132–12136 (1987) with modifications.
    Willcocks, A. L., Cooke, A. M., Potter, B. V. L., and Nahorski, S. R. Stereospecific Recognition Sites for [$^3$H]Inositol (1, 4, 5)-Triphosphate in Particulate Preparations of Rat Cerebellum. Biochem. Biophys. Res. Comm. 147: 1071–1078 (1987).
Results:     Receptor Binding Activity Percent Inhibition Average (N = 2)

| Nicotine $10^{-6}$M | Cotinine $10^{-4}$M | Cotinine $10^{-6}$M | Cotinine$_2$ Fumarate $10^{-6}$M |
|---|---|---|---|
| 3.2% | 8.3% | 4.8% | −5.1% |

In order to provide perspective concerning blood levels of the test compounds employed, the molar concentrations listed above will be related to cigarette consumption. For nicotine, a concentration of $10^{-6}$M equals a blood level of 166 ng/ml, which is a very high smoking dose of about 4–5 packs per day. For cotinine, $10^{-6}$M equals a blood level of 176 ng/ml, or a low smoking dose of about ¼–½ pack per day. Cotinine at $10^{-4}$M equals a blood level of 17,600 ng/ml, which is regarded to be an acceptable therapeutic dose level. Cotinine is so nontoxic that even higher doses can be used for short periods of time.

It has been shown previously that cotinine is capable of passing the blood-brain barrier (U.S. Pat. Nos. 3,870,794 and 5,187,169). The results obtained in the above examples show that the cotinine compounds are, in addition, capable of binding to receptor sites. Cotinine and cotinine fumarate produced neuroleptic activity paralleling nicotine at all of the sites and neurotransmitters tested. In addition, the percent of inhibition for cotinine was numerically greater in 12 of the 16 items investigated. Cotinine therefore usually exhibits greater activity than nicotine at the same dosage. Moreover, since cotinine exhibits virtually no toxicity, it can be used therapeutically at much higher concentrations than nicotine and therefore therapy with cotinine can produce an effect many times greater than therapy with nicotine. In all of the examples presented, cotinine and cotinine fumarate exhibit binding activity that is similar to nicotine and usually of greater magnitude. The significance of this is that the examples therefore demonstrate the similarity of cotinine and cotinine fumarate to nicotine in brain receptor binding assays at the binding sites and transmitters that are important in Tourette's syndrome, obsessive-compulsive behavior and schizophrenia. It is interesting to note that while neither nicotine nor cotinine bind especially to dopamine or serotonin receptors, both compounds are recognized to have dopaminergic and serotonergic activity. Presumably, these effects are pre-synaptic, post-synaptic or indirect. It should also be noted that the neurotransmitters in Examples 10, 11, 13 and 14 are commonly implicated with drugs of abuse. These examples therefore demonstrate therapeutic activity of cotinine in drug abuse.

The examples show that cotinine and cotinine fumarate have a binding activity that is as great as or greater than nicotine, and because cotinine can be used therapeutically in a far higher concentration in the blood, it can provide a much greater therapeutic effect than nicotine. The data from the above examples therefore provides support for cotinine compounds as a treatment for obsessive-compulsive disorder, Tourette's Syndrome and schizophrenia that is more effective than nicotine.

The Effect of Cotinine in Glutamatergic Transmission

McGehee previously reported that the behavioral and cognitive effects of nicotine suggest that nicotinic acetylcholine receptors participate in central nervous system (CNS) function. The complex behavioral effects of nicotine are revealed by the finding that central nervous system nicotinic acetylcholine receptors enhance fast excitatory transmission. In vitro studies also showed that one excitatory CNS transmitter is glutamate. This neurotransmitter is metabolized by the enzyme glutamic acid decarboxylase (GAD). The application of nicotine to the same CNS sites was shown by in vitro studies to enhance glutamatergic transmission since the amplitude of the evoked currents more than doubled [McGehee, et al. "Nicotine Enhancement of Fast Excitatory Synaptic Transmission in CNS by Presynaptic Receptors", Science, 269:1692 (1995)]. Enzyme activity studies conducted by me now show that both cotinine and nicotine have a similar effect on GAD as shown in the following example.

Radioimmunoassay studies were conducted with rat corpus striatal membranes using the following method.

Example 17

Glutamic Acid Decarboxylase (GAD) Enzyme Assay

| Reference Compounds Ki(nM) Assay Characteristics | (Amino-oxy)Acetic Acid | 3,550 |
|---|---|---|
| Degree of Specific Binding: Materials and Methods: | >95% (Non-specific activity determined in the absence of tissue) | |
| Enzyme Source: | Rat corpus striatal membranes | |
| Substrate: | [$^{14}$C]L-Glutamic acid (30–80 Ci/mmol) | |
| Reference Compound: | (Amino-oxy)Acetic Acid | |
| Positive Control: | (Amino-oxy)Acetic Acid | |
| Incubation Conditions: | Reactions are incubated in phosphate/mercapoethanol buffer (pH 6.9) for 30 minutes at 37° C. The reaction is stopped by the addition of trichloroacetic acid and placement on ice. Radioactive product is trapped in phenylethylamine/methanol and quantitated using liquid scintillation chromatography in order to ascertain any interactions of test compounds with the glutamic acid decarboxylase enzyme. Literature references to receptor binding activity procedure: Wilson, S. H., et al. Jrnl. Biol. Chem. 247: 3159 (1972). | |
| Results: | Percent Inhibition | |
| | Nicotine $10^{-8}$M | Cotinine $10^{-8}$M |
| | 40% | 38% |

Example 17 shows that cotinine has about the same inhibitory effect of nicotine with respect to GAD, an enzyme which converts glutamate into gammaaminobutyric acid (GABA). The ratio of glutamic acid to GABA (gammaaminobutyric acid) in the brain plays a crucial role in brain activity. Glutamate is an excitatory transmitter. GABA is an inhibitory transmitter. Furthermore, the concentration of glutamate and GABA are higher in the brain than they are in the rest of the body. The effectiveness of cotinine to inhibit the metabolic enzyme GAD provides further support for its benefit in treating substance abuse or addiction by providing a "feeling good" response which lessens the need to continue the undesired activity or thought pattern. In treating these disorders, cotinine is administered in the same manner outlined above in any desired dosage form as already described. Because cotinine is thought to be innocuous when used by humans, people may be able to use cotinine as long as necessary in an effort to help them treat their particular addition (or behavior) which may have developed over many years.

This sheds light on the effectiveness of cotinine in treating obsessive-compulsive disorder, Tourette's Syndrome and schizophrenia through its ability to inhibit the activity of GAD so as to make the patient feel better, thereby further assisting in alleviating or reducing the symptoms of the disease. Thus, nicotine and cotinine both trigger a molecular switch in the brain that speeds up the flow and intensity of glutamate, a function important in the nicotine-dependency process because it elicits a "feeling-good" response in the person who has consumed the nicotine, but cotinine will produce a therapeutic effect many times greater than nicotine because it can be safely administered in much greater amounts.

The present invention has utility in treating other psychiatric disorders. The data developed in the above examples indicate that the invention is useful in substance addiction generally and, in particular, in treating drug and alcohol addiction so as to alleviate or reduce the symptoms of the disorder and in treating manic-depression syndrome by providing a "feeling good" response when administered as described as above. The invention is also indicated to be useful in alleviating or reducing the symptoms of anorexia and bulimia, which are characterized by a failure to eat appropriate amounts of food or by eating and purging. In these disorders it is the same nicotinic-acetylcholine receptors, as well as others described in the above examples, which are active in the chain of events that current research indicates to be an important factor underlying the disease. The examples demonstrate that cotinine is effective in influencing these receptors and transmitters in an advantageous manner so as to relieve or reduce the symptoms of the disorder. The heavy use of tobacco by drug and alcohol addicts further supports the effectiveness of cotinine in these applications because it is the main metabolite of the nicotine that was consumed. Moreover, anorexia and bulimia are indeed forms of an obsessive-compulsive disorder which are indicated to respond favorably to treatment using the present invention as already noted. Accordingly, bulimia/anorexia patients can benefit from the present invention in a manner similar to patients who suffer from other forms of obsessive-compulsive disorders. It should be noted that behavioral scientists group obsessive-compulsive disorder, Tourette's Syndrome, and anorexia/bulimia together because of their similar neurochemical origins.

Nicotine has been described as a "behavioral homeostat" because it appears to increase "low behavior" and decrease "high behavior" [Rosecrans J. A. "The Role of Nicotine in Tobacco Dependence and Cessation." *Chemistry and Industry, pp.*221–224 (21 Mar. 1994)]. The author explains the mechanism by noting "nicotine's ability to desensitize its receptor." The results of the tests described above indicate that the cotinine metabolized from nicotine, which acts to block the nicotinic cholinergic receptors (in effect desensitizing them), and the dynamic interplay of varying concentrations of nicotine and cotinine in the smoker's brain produces the unusual benefit previously described as a "behavioral homeostat."

All publications and patents are herein incorporated by reference to the same extent as if each individual publication or patent was specifically and individually indicated to be incorporated by reference.

Many variations of the present invention within the scope of the appended claims will be apparent to those skilled in the art once the principles described herein are understood.

What is claimed is:

1. A method of treating a patient suffering from obsessive-compulsive disorder, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of obsessive-compulsive disorder.

2. The method of claim 1 wherein the pharmaceutical agent or said salt is selected from the group consisting of a tablet or capsule, a transdermal delivery system, a chewing gum, an interocular insert, an inhaler and an aqueous solution of cotinine.

3. A method of treating a patient suffering from Tourette's Syndrome, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of Tourette's Syndrome.

4. The method of claim 3 wherein said pharmaceutical agent or said salt is selected from the group consisting of a tablet or capsule, a transdermal delivery system, a chewing gum, an interocular insert, an inhaler and an aqueous solution of cotinine.

5. A method of treating a patient suffering schizophrenia, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of schizophrenia.

6. The method of claim 5 wherein the pharmaceutical agent or said salt is selected from the group consisting of a tablet or capsule, a transdermal delivery system, a chewing gum, an interocular insert, an inhaler and an aqueous solution of cotinine.

7. A method of treating a patient suffering from substance abuse or substance addiction, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of substance abuse or substance addiction.

8. The method of claim 7 wherein the pharmaceutical agent or said salt is selected from the group consisting of a tablet or capsule, a transdermal delivery system, a chewing gum, an interocular insert, an inhaler and an aqueous solution of cotinine.

9. The method of claim 7 wherein the addiction comprises drug or alcohol addiction.

10. The method of claim 9 wherein the pharmaceutical agent or said salt is selected from the group consisting of a tablet or capsule, a transdermal delivery system, a chewing gum, an interocular insert, an inhaler and an aqueous solution of cotinine.

11. A method of treating a patient suffering from manic-depression syndrome, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of manic-depression syndrome.

12. The method of claim 11 wherein the pharmaceutical agent or said salt is selected from the group consisting of a tablet or capsule, a transdermal delivery system, a chewing gum, an interocular insert, an inhaler and an aqueous solution of cotinine.

13. A method of treating a patient suffering from anorexia or bulimia, said method comprising, providing for such a patient a pharmaceutical agent comprising cotinine or a pharmaceutically acceptable salt thereof in a dosage between about 0.5 mg/kg to 100 mg/kg body weight per day for alleviating, in a human in need of such treatment, at least one of the symptoms of anorexia or bulimia.

14. The method of claim 13 wherein the pharmaceutical agent or said salt is selected from the group consisting of a tablet or capsule, a transdermal delivery system, a chewing gum, an interocular insert, an inhaler and an aqueous solution of cotinine.

* * * * *

UNITED STATES PATENT AND TRADEMARK OFFICE
CERTIFICATE OF CORRECTION

PATENT NO. : 5,889,029
DATED : Mar. 30, 1999
INVENTOR(S) : ROLF

It is certified that error appears in the above-indentified patent and that said Letters Patent is hereby corrected as shown below:

Col. 2, line 60, delete "to about 1 µmol/l" and change "one-half-pack-a-day" to ---one-pack-a-day---.

Signed and Sealed this

Eleventh Day of January, 2000

Attest:

Q. TODD DICKINSON

*Attesting Officer*   *Acting Commissioner of Patents and Trademarks*